(12) United States Patent
Gao et al.

(10) Patent No.: US 11,292,998 B2
(45) Date of Patent: Apr. 5, 2022

(54) CULTURE DEVICE AND PREPARATION METHOD FOR A CELL MEMBRANE

(71) Applicant: BOE TECHNOLOGY GROUP CO., LTD., Beijing (CN)

(72) Inventors: Shuang Gao, Beijing (CN); Xin Jin, Beijing (CN); Juan Wang, Beijing (CN); Yufei Zhao, Beijing (CN); Yuqin Tan, Beijing (CN); Zhisheng Li, Beijing (CN); Dehua Chang, Beijing (CN)

(73) Assignee: BOE Technology Group Co., Ltd., Beijing (CN)

( * ) Notice: Subject to any disclaimer, the term of this patent is extended or adjusted under 35 U.S.C. 154(b) by 103 days.

(21) Appl. No.: 16/525,958

(22) Filed: Jul. 30, 2019

(65) Prior Publication Data

US 2020/0332238 A1 Oct. 22, 2020

(30) Foreign Application Priority Data

Apr. 16, 2019 (CN) .......................... 201910303032.1

(51) Int. Cl.
| | |
|---|---|
| *C12M 1/38* | (2006.01) |
| *C12M 3/00* | (2006.01) |
| *C12M 1/34* | (2006.01) |
| *H01L 35/04* | (2006.01) |

(52) U.S. Cl.
CPC ................ *C12M 3/00* (2013.01); *C12M 1/38* (2013.01); *C12M 41/12* (2013.01); *H01L 35/04* (2013.01)

(58) Field of Classification Search
CPC .......... C12M 41/12; C12M 1/38; H01L 35/04
See application file for complete search history.

(56) References Cited

U.S. PATENT DOCUMENTS

| | | | |
|---|---|---|---|
| 8,720,209 B1* | 5/2014 | Beer | ...................... C12M 41/18 62/3.3 |
| 2008/0236643 A1* | 10/2008 | Li | ........................... H01L 35/32 136/203 |
| 2013/0005039 A1* | 1/2013 | Duschl | ................... C12M 25/06 435/377 |
| 2014/0193911 A1 | 7/2014 | Newby et al. | |

FOREIGN PATENT DOCUMENTS

| | | |
|---|---|---|
| CN | 1931065 A | 3/2007 |
| CN | 102174386 A | 9/2011 |
| CN | 102329727 A | 1/2012 |
| CN | 103649305 A | 3/2014 |
| CN | 103794580 A | 5/2014 |

* cited by examiner

*Primary Examiner* — Jonathan M Hurst
(74) *Attorney, Agent, or Firm* — The Webb Law Firm

(57) ABSTRACT

The present disclosure provides a culture device and a preparation method for a cell membrane, and relates to the field of cell culture technology. The culture device for a cell membrane includes a semiconductor refrigerator, and one or more culture vessels configured to culture a cell membrane. The semiconductor refrigerator includes a first insulating substrate, a second insulating substrate, and at least one semiconductor thermocouple disposed between the first insulating substrate and the second insulating substrate. The one or more culture vessels are disposed on a side of the first insulating substrate away from the second insulating substrate.

16 Claims, 4 Drawing Sheets

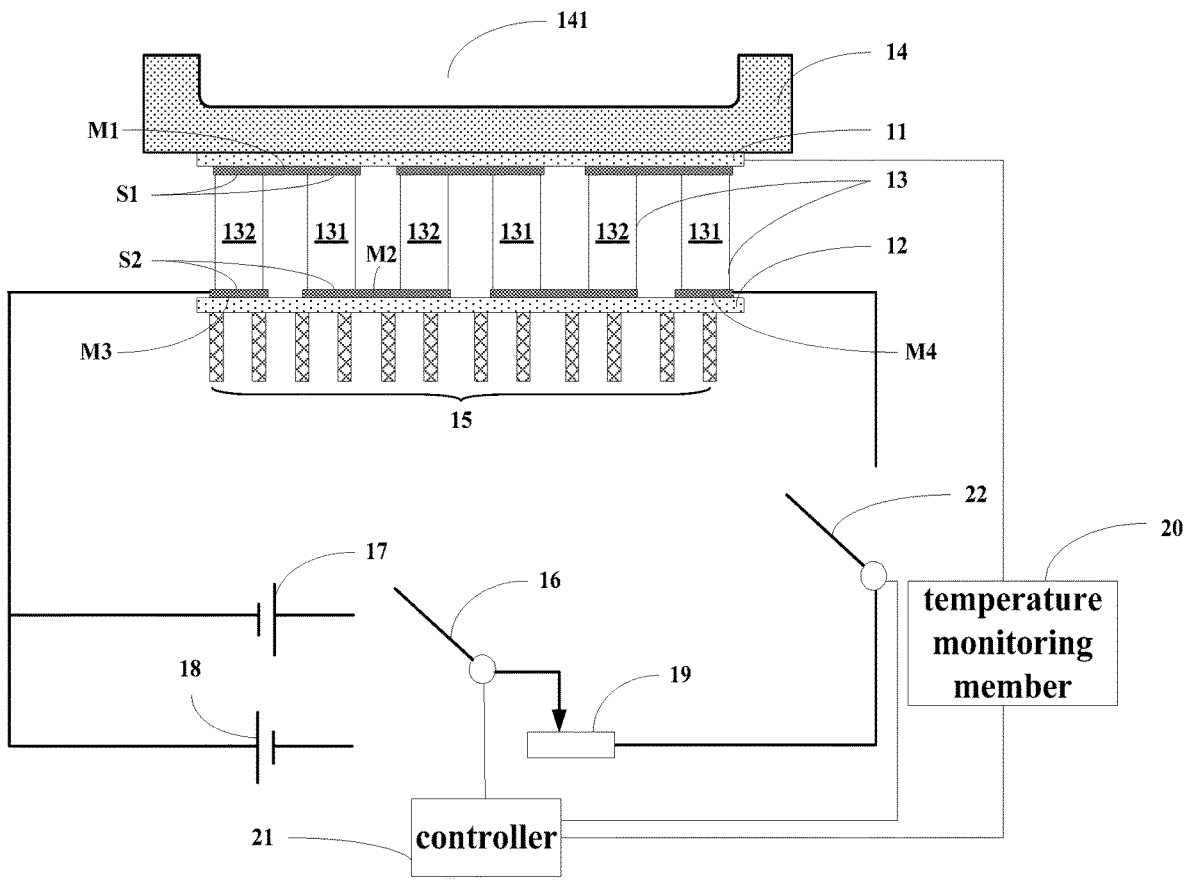

Fig.5

| adjust the first insulating substrate of the semiconductor refrigerator to be of a first temperature to make a plurality of cells in the culture vessel form a cell membrane adsorbed to a temperature-sensitive polymer layer | 602 |

↓

| adjust the first insulating substrate to be of a second temperature different from the first temperature to make the cell membrane separate from the temperature-sensitive polymer layer | 604 |

Fig.6

CULTURE DEVICE AND PREPARATION METHOD FOR A CELL MEMBRANE

CROSS-REFERENCE TO RELATED APPLICATIONS

The present application claims priority to Chinese Patent Application No. 201910303032.1, filed on Apr. 16, 2019, the disclosure of which is incorporated by reference herein in its entirety.

TECHNICAL FIELD

The present disclosure relates to the field of cell culture technology, and especially to a culture device and a preparation method for a cell membrane.

BACKGROUND

The cell membrane is a membrane-like tissue formed by connecting a cell to an extracelluar matrix secreted by the cell. The cell membrane which has a high cell density, a uniform cell distribution, and a uniform texture, may be used for the repair of organs or tissues such as skin, cartilage, cornea, and myocardium.

SUMMARY

According to one aspect of embodiments of the present disclosure, a culture device for a cell membrane is provided. The culture device for a cell membrane comprises: a semiconductor refrigerator, comprising: a first insulating substrate, a second insulating substrate, and at least one semiconductor thermocouple disposed between the first insulating substrate and the second insulating substrate; and one or more culture vessels configured to culture a cell membrane and disposed on a side of the first insulating substrate away from the second insulating substrate.

In some embodiments, the semiconductor refrigerator further comprises: a thermally conductive member disposed on the side of the first insulating substrate away from the second insulating substrate, wherein the one or more culture vessels is disposed on the thermally conductive member.

In some embodiments, the thermally conductive member defines one or more grooves, wherein the one or more culture vessels are disposed in the one or more grooves one to one.

In some embodiments, an orthographic projection of the first insulating substrate on the second insulating substrate is within an orthographic projection of the thermally conductive member on the second insulating substrate.

In some embodiments, a temperature-sensitive polymer layer is disposed on one surface of a bottom, away from the first insulating substrate, of at least one of the one or more culture vessels, wherein a surface energy of the temperature-sensitive polymer layer changes monotonously with changing temperature.

In some embodiments, the surface energy of the temperature-sensitive polymer layer increases with increasing temperature.

In some embodiments, the at least one semiconductor thermocouple comprises N semiconductor thermocouples, where N is an integer greater than or equal to 2, wherein: each of the N semiconductor thermocouples comprises a first semiconductor portion and a second semiconductor portion of different conductive types, wherein each of the first semiconductor portion and the second semiconductor portion comprises a first surface and a second surface opposite to the first surface, the first surface is closer to the first insulating substrate than the second surface, and the first surface of the first semiconductor portion is connected to the first surface of the second semiconductor portion via a first metal member, and the second surface of the first semiconductor portion of the i-th semiconductor thermocouple is connected to the second surface of the second semiconductor portion of the (i+1)-th semiconductor thermocouple via a second metal member, wherein $1 \leq i \leq N-1$.

In some embodiments, the semiconductor refrigerator further comprises a first switch, a first power supply, and a second power supply, wherein: a first pole of the first power supply is connected to the second surface of the second semiconductor portion of a first semiconductor thermocouple via a third metal member, and a second pole of the first power supply is configured to be connected to the second surface of the first semiconductor portion of an N-th semiconductor thermocouple via the first switch and a fourth metal member, wherein one of the first pole and the second pole is a positive pole and the other is a negative pole; the second pole of the second power supply is connected to the second surface of the second semiconductor portion of the first semiconductor thermocouple via the third metal member, and the first pole of the second power supply is configured to be connected to the second surface of the first semiconductor portion of the N-th semiconductor thermocouple via the first switch and the fourth metal member; the first switch is configured to be connected to one of the second pole of the first power supply and the first pole of the second power supply in response to a user operation.

In some embodiments, the semiconductor refrigerator further comprises: a temperature monitoring member configured to monitor a temperature of the first insulating substrate; and a controller configured to control a state of the first switch according to the temperature of the first insulating substrate.

In some embodiments, the controller is configured to: control the first switch to be ON in a case where the temperature of the first insulating substrate is within a preset temperature range; control the first switch to be OFF, or to switch from connection to one of the second pole of the first power supply and the first pole of the second power supply to connection to the other in a case where the temperature of the first insulating substrate is not within the preset temperature range.

In some embodiments, the semiconductor refrigerator further comprises: a second switch connected between the first power supply and the N semiconductor thermocouples, and connected between the second power supply and the N semiconductor thermocouples; wherein the controller is configured to: control the first switch and the second switch to be ON in a case where the temperature of the first insulating substrate is within a preset temperature range; control at least one of the first switch or the second switch to be OFF in a case where the temperature of the first insulating substrate is not within the preset temperature range.

In some embodiments, the semiconductor refrigerator further comprises: a voltage dividing tunable element connected between the first power supply and the N semiconductor thermocouples, and connected between the second power supply and the N semiconductor thermocouples.

In some embodiments, the semiconductor refrigerator further comprises: a heat dissipating member disposed on a side of the second insulating substrate away from the first insulating substrate.

In some embodiments, the semiconductor refrigerator is disposed separately from the one or more culture vessels.

According to another aspect of embodiments of the present disclosure, a preparation method for a cell membrane based on a culture device for a cell membrane is provided. The culture device for the cell membrane comprises: a semiconductor refrigerator comprising a first insulating substrate, a second insulating substrate, and at least one semiconductor thermocouple disposed between the first insulating substrate and the second insulating substrate; and one or more culture vessels disposed on a side of the first insulating substrate away from the second insulating substrate, a temperature-sensitive polymer layer is disposed on one surface of a bottom, away from the first insulating substrate, of at least one of the one or more culture vessels, wherein a surface energy of the temperature-sensitive polymer layer changes monotonously with changing temperature. The preparation method comprises: adjusting the first insulating substrate to be of a first temperature to make a plurality of cells in at least one of the one or more culture vessels form the cell membrane adsorbed to the temperature-sensitive polymer layer; and adjusting the first insulating substrate to be of a second temperature different from the first temperature to make the formed cell membrane separate from the temperature-sensitive polymer layer.

In some embodiments, the second temperature is less than the first temperature.

According to still another aspect of embodiments of the present disclosure, a preparation method for a cell membrane based on a culture device for a cell membrane is provided. The culture device for a cell membrane comprises: a semiconductor refrigerator comprising a first insulating substrate, a second insulating substrate, and at least one semiconductor thermocouple disposed between the first insulating substrate and the second insulating substrate; and one or more culture vessels disposed on a side of the first insulating substrate away from the second insulating substrate. The preparation method comprises: forming a temperature-sensitive polymer layer on one surface of a bottom, away from the first insulating substrate, of at least one of the one or more culture vessels, wherein a surface energy of the temperature-sensitive polymer layer changes monotonously with changing temperature; adjusting the first insulating substrate to be of a first temperature to make a plurality of cells in at least one of the one or more culture vessels form the cell membrane adsorbed to the temperature-sensitive polymer layer; and adjusting the first insulating substrate to be of a second temperature different from the first temperature to make the formed cell membrane separate from the temperature-sensitive polymer layer.

In some embodiments, the second temperature is less than the first temperature.

Other features, aspects and advantages of the present disclosure will become apparent from the following detailed description of exemplary embodiments of the present disclosure with reference to the accompanying drawings.

BRIEF DESCRIPTION OF THE DRAWINGS

The accompanying drawings, which constitute part of this specification, illustrate exemplary embodiments of the present disclosure and, together with this specification, serve to explain the principles of the present disclosure, in which:

FIG. 5 is a schematic structural view showing a semiconductor refrigerator according to yet another implementation of the present disclosure;

FIG. 6 is a schematic flow chart showing a preparation method for a cell membrane according to an embodiment of the present disclosure.

Figure 1:
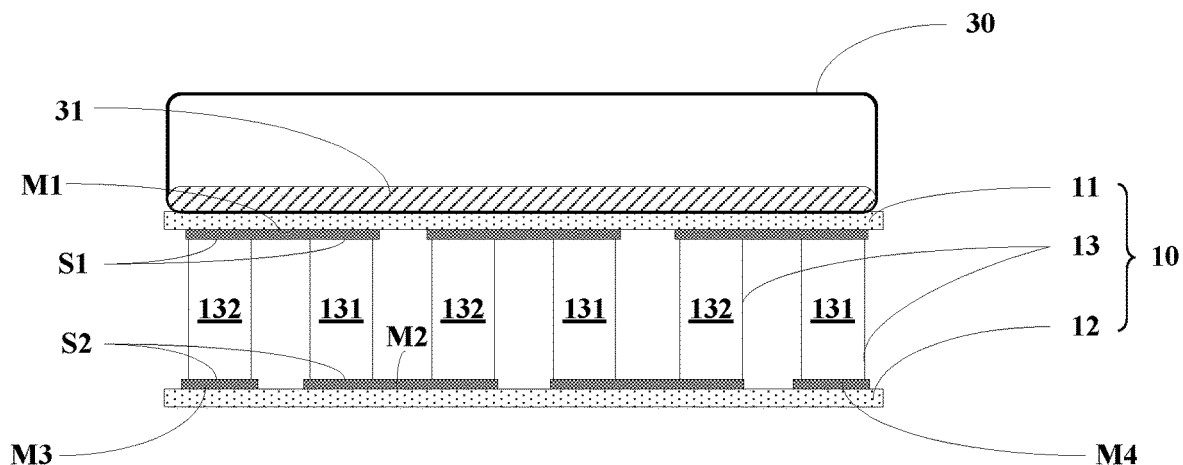
FIG. 1 is a schematic structural view showing a culture device for a cell membrane according to an embodiment of the present disclosure.

It should be understood that the dimensions of the various parts shown in the accompanying drawings are not necessarily drawn according to the actual scale. In addition, the same or similar reference signs are used to denote the same or similar components.

DETAILED DESCRIPTION

Various exemplary embodiments of the present disclosure will now be described in detail with reference to the accompanying drawings. The following description of the exemplary embodiments is merely illustrative and is in no way intended as a limitation to the present disclosure, its application or use. The present disclosure may be implemented in many different forms, which are not limited to the embodiments described herein. These embodiments are provided to make the present disclosure thorough and complete, and fully convey the scope of the present disclosure to those skilled in the art. It should be noticed that: relative arrangement of components and steps, material composition, numerical expressions, and numerical values set forth in these embodiments, unless specifically stated otherwise, should be explained as merely illustrative, and not as a limitation.

The use of the terms "first", "second" and similar words in the present disclosure do not denote any order, quantity or importance, but are merely used to distinguish between different parts. A word such as "comprise", "have" or variants thereof means that the element before the word covers the element(s) listed after the word without excluding the possibility of also covering other elements. The terms "up", "down", or the like are used only to represent a relative positional relationship, and the relative positional relationship may be changed correspondingly if the absolute position of the described object changes.

In the present disclosure, when it is described that a specific component is disposed between a first component and a second component, there may be an intervening component between the specific component and the first component or between the specific component and the second component. When it is described that a specific part is connected to other parts, the specific part may be directly connected to the other parts without an intervening part, or not directly connected to the other parts with an intervening part.

Unless otherwise defined, all terms (comprising technical and scientific terms) used herein have the same meanings as the meanings commonly understood by one of ordinary skill in the art to which the present disclosure belongs. It should also be understood that terms as defined in general dictionaries, unless explicitly defined herein, should be interpreted as having meanings that are consistent with their meanings in the context of the relevant art, and not to be interpreted in an idealized or extremely formalized sense.

Techniques, methods, and apparatus known to those of ordinary skill in the relevant art may not be discussed in detail, but where appropriate, these techniques, methods, and apparatuses should be considered as part of this specification.

In the related art, a cell membrane may be prepared by using a temperature-sensitive culture dish coated with a temperature-sensitive polymer layer. When a cell membrane is prepared, it is necessary to adjust a temperature of the temperature-sensitive culture dish.

Embodiments of the present disclosure propose to combine semiconductor refrigeration technology with the preparation of a cell membrane, which will be described below with reference to different embodiments.

FIG. 1 is a schematic structural view showing a culture device for a cell membrane according to an embodiment of the present disclosure.

As shown in FIG. 1, the culture device for a cell membrane may comprise a semiconductor refrigerator 10, and one or more culture vessels 30. Here, FIG. 1 only schematically shows one culture vessel 30.

The culture vessel 30 is configured to culture a cell membrane. The semiconductor refrigerator 10 is configured to adjust a temperature of the culture vessel 30.

The semiconductor refrigerator 10 comprises a first insulating substrate 11, a second insulating substrate 12, and at least one semiconductor thermocouple 13. The semiconductor thermocouple 13 is disposed between the first insulating substrate 11 and the second insulating substrate 12. In some embodiments, the semiconductor refrigerator 10 may comprise N semiconductor thermocouples 13, where N is an integer greater than or equal to 2. Here, FIG. 1 schematically shows three semiconductor thermocouples 13.

Referring to FIG. 1, each of the N semiconductor thermocouples 13 may comprise a first semiconductor portion 131 and a second semiconductor portion 132 of different conductive types. In some embodiments, an insulating material may be filled between the first semiconductor portion 131 and the second semiconductor portion 132. For example, the first semiconductor portion 131 is an N-type semiconductor, and the second semiconductor portion 132 is a P-type semiconductor. For another example, the first semiconductor portion 131 is a P-type semiconductor, and the second semiconductor portion 132 is an N-type semiconductor.

Each of the first semiconductor portion 131 and the second semiconductor portion 132 comprises a first surface S1 and a second surface S2 opposite to first surface S1. Here, the first surface S1 is closer to the first insulating substrate 11 than the second surface S2. Taking the first semiconductor portion 131 as an example, referring to FIG. 1, the first surface S1 of the first semiconductor portion 131 may be, for example, an upper surface of the first semiconductor portion 131, and the second surface S2 of the first semiconductor portion 131 may be, for example, the lower surface of the first semiconductor portion 131.

The first surface S1 of the first semiconductor portion 131 may be connected to the first surface S1 of the second semiconductor portion 132 via the first metal member M1. The material of the first metal member M1 may comprise, for example, copper, iron, aluminum, or an alloy of the foregoing materials or the like.

The second surface S2 of the first semiconductor portion 131 of i-th semiconductor thermocouple 13 is connected to the second surface S2 of the second semiconductor portion 132 of the (i+1)-th semiconductor thermocouple 13 via a second metal member M2. Here, $1 \leq i \leq N-1$. The material of the second metal member M2 may comprise, for example, copper, iron, aluminum, or an alloy of the foregoing materials or the like. For example, the first semiconductor thermocouple 13 may be the leftmost semiconductor thermocouple 13, and the N-th semiconductor thermocouple 13 may be the rightmost semiconductor thermocouple 13, or vice versa.

In a case where the semiconductor thermocouple 13 is connected into a loop, one of the first insulating substrate 11 and the second insulating substrate 12 is a cold end and the other is a hot end according to the Peltier effect. In some embodiments, the material of each of the first insulating substrate 11 and the second insulating substrate 12 may comprise, but is not limited to, ceramic material of a favorable thermal conductive property and being electrically insulated.

The culture vessel 30 is disposed on a side of the first insulating substrate 11 away from the second insulating substrate 12. In some embodiments, the culture vessel 30 may comprise, for example, but is not limited to, a culture dish, a culture flask, a culture plate, or the like. As some implementations, the shape of the culture vessel 30 may comprise, but is not limited to, a circle, a square, or the like.

In some implementations, the semiconductor refrigerator 10 and the culture vessel 30 may be fixed together. For example, the culture vessel 30 may be fixed together with the first insulating substrate 11. In other implementations, the semiconductor refrigerator 10 may be disposed separately from the culture vessel 30, i.e. the semiconductor refrigerator 10 is not fixed together with the culture vessel 30.

In some embodiments, a temperature-sensitive polymer layer 31 is disposed on one surface, away from the first insulating substrate 11, of a bottom of at least one culture vessel 30. Here, a surface energy of the temperature-sensitive polymer layer 31 changes monotonously with changing temperature, for example increases or decreases with increasing temperature.

In some implementations, the surface energy of the temperature-sensitive polymer layer 31 may increase with increasing temperature. For example, the molecular chain structure of the temperature-sensitive polymer exhibits a curled shape at a high temperature suitable for cell culture (e.g., about 37° C.). In this case, the temperature-sensitive polymer which has a high surface energy and exhibits a hydrophobic property is favorable for cell adhesion. The molecular chain structure of the temperature-sensitive polymer exhibits a stretched shape at a low temperature (e.g., from about 15° C. to about 25° C.). In this case, the temperature-sensitive polymer which has a low surface energy and exhibits a hydrophilic property is unfavorable for cell adhesion. As an example, the material of the temperature-sensitive polymer layer 31 may comprise one or more of the following materials: poly (N-isopropylacrylamide), poly (N-n-propylacrylamide).

In other implementations, the surface energy of the temperature-sensitive polymer layer 31 may decrease with increasing temperature.

When a cell membrane is prepared by the above culture device for a cell membrane, the temperature of the first insulating substrate of the semiconductor refrigerator may be adjusted to make the culture vessel being at a temperature suitable for a cell membrane to form, thus a cell membrane adsorbed to the temperature-sensitive polymer layer is formed. Further, the temperature of the first insulating substrate of the semiconductor refrigerator may be adjusted again to make the culture vessel being at a temperature suitable for a cell membrane to separate from the temperature-sensitive polymer layer, thus a cell membrane is obtained. The cell membrane obtained in this manner is not treated with enzyme and its analogues, and retains the extracellular matrix secreted by cell proliferation.

The semiconductor refrigerator is used to adjust the temperature of the culture vessel. On one aspect, the influence of the ambient temperature on the temperature of the culture vessel is alleviated, and the temperature of the culture vessel is adjusted more accurately. In another aspect, the cooling or heating speed of the semiconductor refrigerator is fast, and the temperature of the culture vessel is adjusted more quickly. In still another aspect, the semiconductor refrigerator is likely to be miniaturized, and the culture device for a cell membrane may be used in a scene, such as a super clean bench or a biological safety cabinet, where space is limited and cell manipulation is performed.

Figure 2:
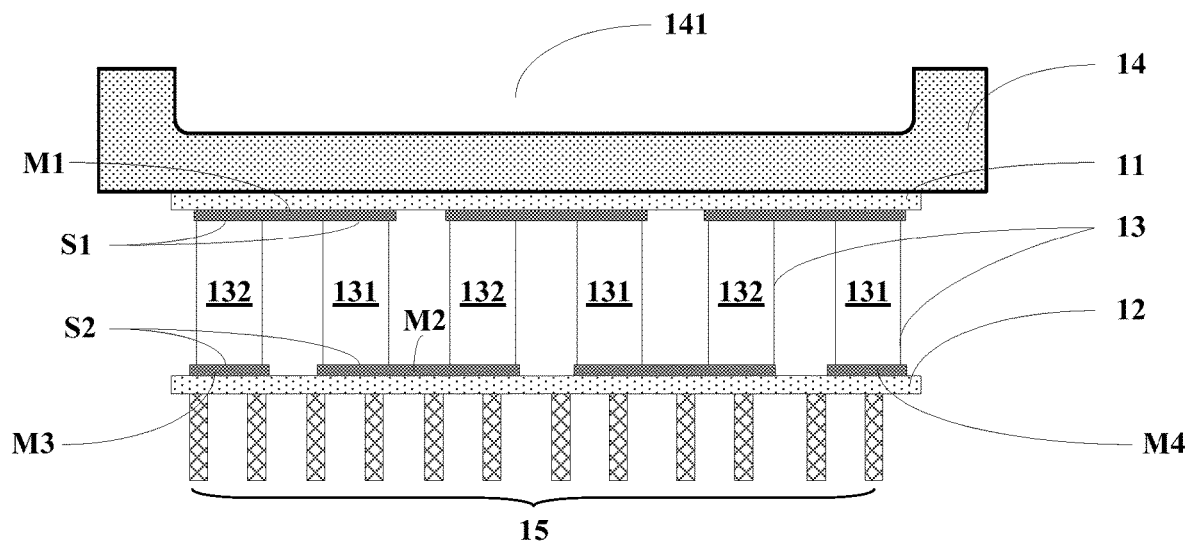
FIG. 2 is a schematic structural view showing a semiconductor refrigerator according to an implementation of the present disclosure.

FIG. 2 is a schematic structural view showing a semiconductor refrigerator according to an implementation of the present disclosure.

The semiconductor refrigerator 10 shown in FIG. 2 further comprises a thermally conductive member 14 compared to the semiconductor refrigerator 10 shown in FIG. 1. The thermally conductive member 14 is disposed on a side of the first insulating substrate 11 away from the second insulating substrate 12. For example, the thermally conductive member 14 may be in direct contact with the first insulating substrate 11. For another example, the thermally conductive member 14 may be adhered to the first insulating substrate 11 by a thermally conductive silicone or the like to improve the heat conduction effect. In some embodiments, the material of the thermally conductive member 14 may comprise, but is not limited to, a metallic material, a polymeric material, an inorganic non-metallic material, or a composite material of the above materials, or the like.

The thermally conductive member 14 facilitates heat transfer between the semiconductor refrigerator 10 and the culture vessel 30, thus the temperature of the culture vessel 30 may be adjusted more quickly by the semiconductor refrigerator 10.

One or more culture vessels 30 may be disposed on the thermally conductive member 14.

In some implementations, the culture vessel 30 may be disposed directly on the surface of the thermally conductive member 14.

In other implementations, as shown in FIG. 2, the thermally conductive member 14 may have one or more grooves 141. At least one culture vessel 30 may be at least partially disposed in the groove 141. For example, the one or more culture vessels 30 are disposed in the one or more grooves one to one the one. As an example, the thermally conductive member 14 may define a plurality of grooves 141 of different sizes in which different sizes of culture vessels 30 may be disposed. The influence of the ambient temperature on the temperature of culture vessel 30 may be further reduced and the temperature of the culture vessel 30 may be adjusted more accurately as the culture vessel 30 is disposed in the groove 141 of the thermally conductive member 14.

In some embodiments, an orthographic projection of the first insulating substrate 11 on the second insulating substrate 12 is within an orthographic projection of the thermally conductive member 14 on the second insulating substrate 12. In this manner, the number of the semiconductor thermocouples 13 in the semiconductor refrigerator 10 and the size of the first insulating substrate 11 in the semiconductor refrigerator 10 may be reduced, thus the semiconductor refrigerator 10 is more portable.

In some embodiments, the semiconductor refrigerator 10 may also comprise a heat dissipating member 15, such as a heat sink. The heat dissipating member is disposed on a side of the second insulating substrate 12 away from the first insulating substrate 11. The heat radiating member 15 may be in direct contact with the second insulating substrate 12, or may be adhered to the second insulating substrate 12 by a thermally conductive silicone or the like. The heat dissipating member 15 facilitates dissipating heat of the second insulating substrate 12, and reducing an adverse effect caused by heat accumulation of the second insulating substrate 12 on the performance of the semiconductor refrigerator 10.

Figure 3:
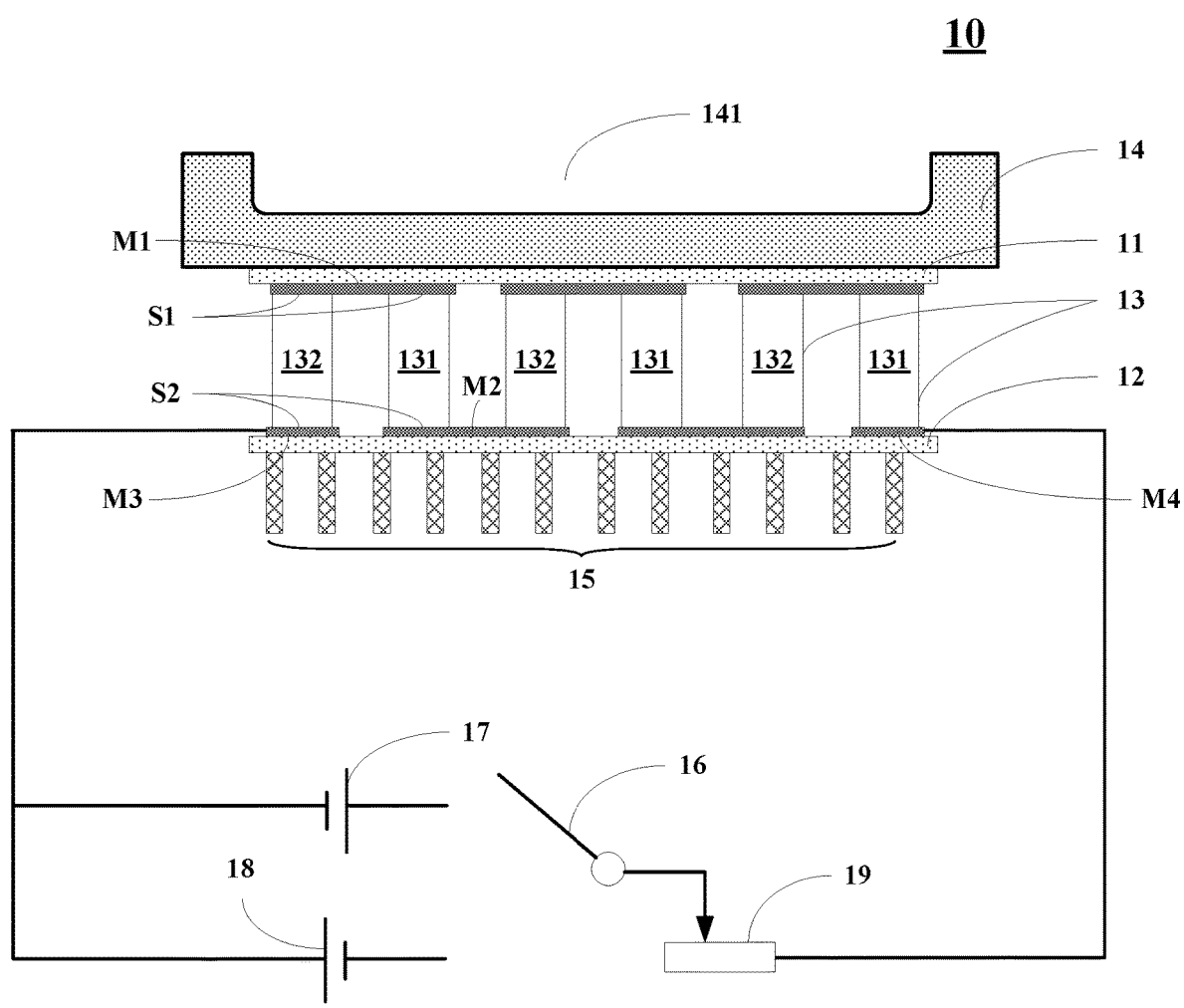
FIG. 3 is a schematic structural view showing a semiconductor refrigerator according to another implementation of the present disclosure.

FIG. 3 is a schematic structural view showing a semiconductor refrigerator according to another implementation of the present disclosure.

The semiconductor refrigerator 10 shown in FIG. 3 further comprises a first switch 16, a first power supply 17, and a second power supply 18 compared to the semiconductor refrigerator 10 shown in FIG. 2. It should be noted that, one of the first pole and the second pole mentioned below is a positive pole and the other is a negative pole. For example, in a case where the first pole is a positive pole, the second pole is a negative pole, or vice versa.

The first pole (for example a negative pole) of the first power supply 17 is connected to the second surface S2 of the second semiconductor portion 132 of the first semiconductor thermocouple 13 via a third metal member M3. The second pole (for example a positive pole) of the first power supply 17 is configured to be connected to the second surface S2 of a first semiconductor portion 131 of an N-th semiconductor thermocouple 13 via the first switch 16 and a fourth metal member M4.

The second pole (for example a positive pole) of the second power supply 18 is connected to the second surface S2 of the second semiconductor portion 132 of the first semiconductor thermocouple 13 via the third metal member M3. The first pole (for example a negative pole) of the second power supply 18 is configured to be connected to the second surface S2 of the first semiconductor portion 131 of the N-th semiconductor thermocouple 13 via the first switch 16 and the fourth metal member M4.

The first switch 16 is configured to be connected to one of the second pole (for example a negative pole) of the first power supply 17 or the first pole (for example a positive pole) of the second power supply 18 in response to a user operation. In other words, the first switch 16 may be connected to the second pole of the first power supply 17 or to the first pole of the second power supply 18 according to a user's operation.

In a case where the first semiconductor portion 131 is an N-type semiconductor and the second semiconductor portion 132 is a P-type semiconductor, the temperature of the culture vessel 30 can be lowered by controlling the first switch 16 to connect to the second pole of the first power supply 17, and can be raised by controlling the first switch 16 to connect to the first pole of the second power supply 18.

In a case where the first semiconductor portion 131 is a P-type semiconductor and the second semiconductor portion 132 is an N-type semiconductor, the temperature of the culture vessel 30 may be lowered by controlling the first switch 16 to connect to the first pole of the second power supply 18, and can be raised by controlling the first switch 16 to connect to the second pole of the first power supply 17.

In some embodiments, at least one of the first metal member M1, the second metal member M2, the third metal member M3, or the fourth metal member M4 described above may be a metal sheet.

In some embodiments, referring to FIG. 3, the semiconductor refrigerator 10 may further comprise a voltage dividing tunable element 19, such as a slide resistor or the like. The voltage dividing tunable element 19 may be provided integrally with the first switch 16. For example, the voltage dividing tunable element 19 may be a voltage divider with a switch. However, the present disclosure is not limited thereto, and the voltage dividing tunable element 19 may also be provided separately from the first switch 16.

The voltage dividing tunable element 19 is connected between the first power supply 17 and the N semiconductor thermocouples 13, and connected between the second power supply 18 and the N semiconductor thermocouples 13. For example, the voltage dividing tunable element 19 may be connected between the negative pole of the first power supply 17 and the first semiconductor thermocouple 13, and connected between the positive pole of the second power supply 18 and the first semiconductor thermocouple 13. For another example, the voltage dividing tunable element 19 is connected between the positive pole of the first power supply 17 and the N-th semiconductor thermocouple 13, and connected between the negative pole of the second power supply 18 and the N-th semiconductor thermocouples 13, as shown in FIG. 3.

In the above embodiments, the voltage applied between two ends of the N semiconductor thermocouples may be changed by the voltage dividing tunable element, thus the cooling or heating speed of the semiconductor refrigerator may be controlled.

Figure 4:
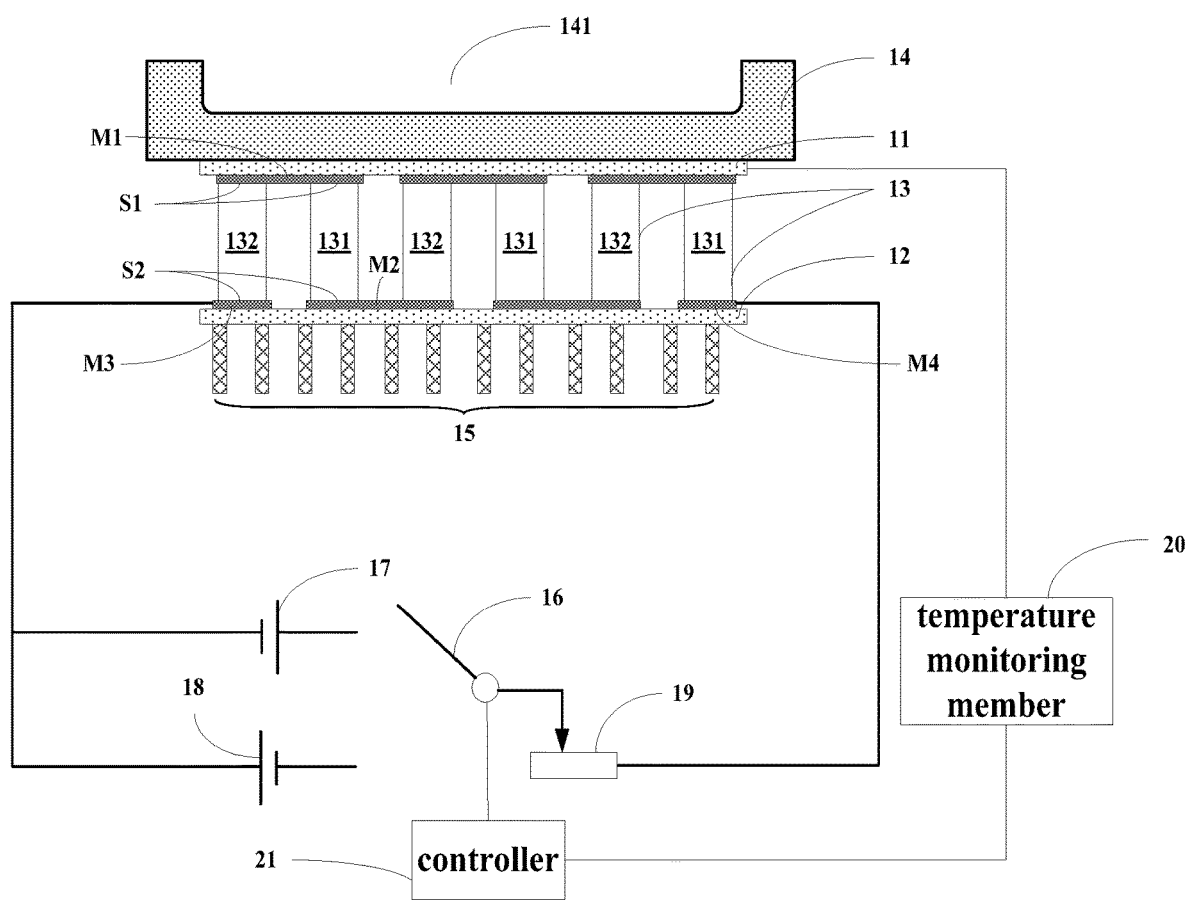
FIG. 4 is a schematic structural view showing a semiconductor refrigerator according to still another implementation of the present disclosure.

FIG. 4 is a schematic structural view showing a semiconductor refrigerator according to a still another implementation of the present disclosure.

The semiconductor refrigerator 10 shown in FIG. 4 may further comprise a temperature monitoring member 20 and a controller 21 compared to the semiconductor refrigerator 10 shown in FIG. 3. The temperature monitoring member 20 is configured to monitor a temperature of the first insulating substrate 11. The controller 21 is configured to control a state of the first switch 16 according to the temperature of the first insulating substrate 11. As an example, the temperature monitoring member 20 may be, for example, a bimetal thermometer or a liquid thermometer.

For example, the controller 21 may be configured to control the first switch 16 to be ON, that is, connect to one of the second pole of the first power supply 17 and the first pole of the second power supply 18, in a case where the temperature of the first insulating substrate 11 is within a preset temperature range. The controller 21 may also be configured to control the first switch to be OFF, i.e. connect to neither of the second pole of the first power supply 17 nor the first pole of the second power supply 18, in a case where a temperature of the first insulating substrate 11 is not within the preset temperature range. The controller 21 may also be configured to control the first switch 16 to shift from connection to one of a second pole of the first power supply 17 and a first pole of the second power supply 18 to connection to the other in a case where a temperature of the first insulating substrate 11 is not within the preset temperature range. It should be understood that the above preset temperature range may be set according to actual conditions.

It is assumed that the first switch 16 is connected to the second pole of the first power supply 17 in a case where the temperature of the first insulating substrate 11 is within the preset temperature range. In a case where the temperature of the first insulating substrate 11 is not within the preset temperature range, the first switch 16 may be controlled by the controller 21 to disconnect to the second pole of the first power supply 17 and not connect to the first pole of the second power supply 18, or shift from connection to the second pole of the first power supply 17 to connection to the first pole of the second power supply 18.

FIG. 5 is a schematic structural view showing a semiconductor refrigerator according to yet another implementation of the present disclosure.

The semiconductor refrigerator 10 shown in FIG. 5 may further comprise a second switch 22 compared to the semiconductor refrigerator 10 shown in FIG. 4. In some embodiments, the second switch 22 may be integrally provided with the temperature monitoring member 20. The second switch 22 is connected between the first power supply 17 and the N semiconductor thermocouples 13, and connected between the second power supply 18 and the N semiconductor thermocouples 13. For example, the second switch 22 may be connected between the negative pole of the first power supply 17 and the first semiconductor thermocouple 13, and connected between the positive pole of the second power supply 18 and the first semiconductor thermocouple 13. For another example, the second switch 22 may be connected between the positive pole of the first power supply 17 and the N-th semiconductor thermocouple 13, and connected between the negative pole of the second power supply 18 and the N-th semiconductor thermocouples 13, as shown in FIG. 5.

In FIG. 5, the controller 15 is configured to: control the first switch 16 and the second switch 22 to be ON in a case where the temperature of the first insulating substrate 11 is within a preset temperature range; and control at least one of the first switch 16 or the second switch 22 to be OFF in a case where the temperature of the first insulating substrate 11 is not within the preset temperature range. For example, in a case where the temperature of the first insulating substrate 11 is within a preset temperature range, the controller 21 controls the first switch 16 to connect to the second pole of the first power supply 17 and the second switch 22 to be ON. In a case where the temperature of the first insulating substrate 11 is not within the preset temperature range, the controller 21 may only control the first switch 16 to disconnect to the second pole of the first power supply 17, or may only control the second switch 22 to be OFF, or may control the first switch 16 to disconnect to the second pole of the first power supply 17 and the second switch 22 to be OFF.

In some embodiments, the semiconductor refrigerator 10 may further comprise a display configured to display the temperature of the first insulating substrate 11. Here, the temperature displayed by the display may comprise degrees Celsius, Fahrenheit, Lord Kelvin, or the like. In some embodiments, the display may also be configured to convert between different types of temperatures.

In some embodiments, the display may be a touch display. A user using the culture device for a cell membrane may, by touch operation, change the state of the first switch 16 or the second switch 22, or adjust voltage division of the voltage dividing adjustable element 19.

In other embodiments, the semiconductor refrigerator 10 may also comprise an operable member such as a knob, a button, or the like. A user using the culture device for a cell membrane may, by operating the operable member, change the state of the first switch 16 or the second switch 22, or adjust voltage division of the voltage dividing adjustable element 19. For example, the first switch 16 may be connected to the second pole of the first power supply 17 by operating a knob, and connected to the first pole of the second power supply 18 by operating another knob.

FIG. 6 is a schematic flow chart showing a preparation method for a cell membrane according to an embodiment of the present disclosure. The preparation method of a cell membrane may be implemented based on the culture device for a cell membrane according to any of the above embodiments.

As shown in FIG. 6, the preparation method for a cell membrane may comprise step 602 and step 604.

At step 602, the first insulating substrate of the semiconductor refrigerator is adjusted to be of a first temperature to make a plurality of cells in the culture vessel form a cell membrane adsorbed to a temperature-sensitive polymer layer.

Here, the plurality of cells may be cells of a mammal, or avian. The first temperature may be adjusted according to cell type. For example, the first temperature may range from about 37° C. to about 38° C.

In some embodiments, a temperature-sensitive polymer layer is disposed at the bottom of the culture vessel. In this case, a culture solution containing a plurality of cells may be directly applied to the culture vessel, and then the first insulating substrate of the semiconductor refrigerator is adjusted to be of the first temperature.

In other embodiments, a temperature-sensitive polymer layer is not disposed at the bottom of the culture vessel. In this case, a temperature-sensitive polymer layer is formed first at the bottom of the culture vessel, then a culture solution containing a plurality of cells is applied to the culture vessel, and afterwards the first insulating substrate of the semiconductor refrigerator is adjusted to of the first temperature.

At step 604, the first insulating substrate is adjusted to be of a second temperature different from the first temperature to make the cell membrane separate from the temperature-sensitive polymer layer.

In some embodiments, the second temperature may be less than the first temperature. For example, the second temperature may range from about 15° C. to about 25° C.

In the above embodiments, the semiconductor refrigerator is used to adjust the temperature of the culture vessel. On one hand, the influence of the ambient temperature on the temperature of the culture vessel is alleviated, and the temperature of the culture vessel is adjusted more accurately. On the other hand, the cooling or heating speed of the semiconductor refrigerator is fast, and the temperature of the culture vessel is adjusted more quickly.

Hereto, various embodiments of the present disclosure have been described in detail. Some details well known in the art are not described to avoid obscuring the concept of the present disclosure. According to the above description, those skilled in the art would fully know how to implement the technical solutions disclosed herein.

Although some specific embodiments of the present disclosure have been described in detail by way of examples, those skilled in the art should understand that the above examples are only for the purpose of illustration and are not intended to limit the scope of the present disclosure. It should be understood by those skilled in the art that modifications to the above embodiments and equivalently substitution of part of the technical features can be made without departing from the scope and spirit of the present disclosure. The scope of the disclosure is defined by the following claims.

What is claimed is:

1. A culture device for a cell membrane, comprising:
a semiconductor refrigerator, comprising:
a first insulating substrate,
a second insulating substrate, and
at least one semiconductor thermocouple disposed between the first insulating substrate and the second insulating substrate, wherein the at least one semiconductor thermocouple comprises N semiconductor thermocouples, where N is an integer greater than or equal to 2, wherein:
each of the N semiconductor thermocouples comprises a first semiconductor portion and a second semiconductor portion of different conductive types, wherein each of the first semiconductor portion and the second semiconductor portion comprises a first surface and a second surface opposite to the first surface, the first surface is closer to the first insulating substrate than the second surface, and the first surface of the first semiconductor portion is connected to the first surface of the second semiconductor portion via a first metal member, and
the second surface of the first semiconductor portion of the i-th semiconductor thermocouple is connected to the second surface of the second semiconductor portion of the (i+1)-th semiconductor thermocouple via a second metal member, wherein $1 \leq i \leq N-1$; and
one or more culture vessels configured to culture a cell membrane and disposed on a side of the first insulating substrate away from the second insulating substrate;
wherein the semiconductor refrigerator further comprises a first switch, a first power supply, and a second power supply, wherein:
a first pole of the first power supply is connected to the second surface of the second semiconductor portion of a first semiconductor thermocouple via a third metal member, and a second pole of the first power supply is configured to be connected to the second surface of the first semiconductor portion of an N-th semiconductor thermocouple via the first switch and a fourth metal member, wherein one of the first pole and the second pole is a positive pole and the other is a negative pole;
wherein the second pole of the second power supply is connected to the second surface of the second semiconductor portion of the first semiconductor thermocouple via the third metal member, and the first pole of the second power supply is configured to be connected to the second surface of the first semiconductor portion of the N-th semiconductor thermocouple via the first switch and the fourth metal member; and
wherein the first switch is configured to be connected to one of the second pole of the first power supply and the first pole of the second power supply in response to a user operation.

2. The culture device for a cell membrane according to claim 1, wherein the semiconductor refrigerator further comprises:
a thermally conductive member disposed on the side of the first insulating substrate away from the second insulating substrate, wherein the one or more culture vessels is disposed on the thermally conductive member.

3. The culture device for a cell membrane according to claim 2, wherein the thermally conductive member defines one or more grooves, wherein the one or more culture vessels are disposed in the one or more grooves one to one.

4. The culture device for a cell membrane according to claim 2, wherein an orthographic projection of the first insulating substrate on the second insulating substrate is within an orthographic projection of the thermally conductive member on the second insulating substrate.

5. The culture device for a cell membrane according to claim 1, wherein a temperature-sensitive polymer layer is disposed on one surface of a bottom, away from the first insulating substrate, of at least one of the one or more culture vessels, wherein a surface energy of the temperature-sensitive polymer layer changes monotonously with changing temperature.

6. The culture device for a cell membrane according to claim 5, wherein the surface energy of the temperature-sensitive polymer layer increases with increasing temperature.

7. The culture device for a cell membrane according to claim 1, wherein the semiconductor refrigerator further comprises:
   a temperature monitoring member configured to monitor a temperature of the first insulating substrate; and
   a controller configured to control a state of the first switch according to the temperature of the first insulating substrate.

8. The culture device for a cell membrane according to claim 7, wherein the controller is configured to:
   control the first switch to be ON in a case where the temperature of the first insulating substrate is within a preset temperature range;
   control the first switch to be OFF, or to switch from connection to one of the second pole of the first power supply and the first pole of the second power supply to connection to the other in a case where the temperature of the first insulating substrate is not within the preset temperature range.

9. The culture device for a cell membrane according to claim 7, wherein the semiconductor refrigerator further comprises:
   a second switch connected between the first power supply and the N semiconductor thermocouples, and connected between the second power supply and the N semiconductor thermocouples;
   wherein the controller is configured to:
   control the first switch and the second switch to be ON in a case where the temperature of the first insulating substrate is within a preset temperature range;
   control at least one of the first switch or the second switch to be OFF in a case where the temperature of the first insulating substrate is not within the preset temperature range.

10. The culture device for a cell membrane according to claim 1, wherein the semiconductor refrigerator further comprises:
    a voltage dividing tunable element connected between the first power supply and the N semiconductor thermocouples, and connected between the second power supply and the N semiconductor thermocouples.

11. The culture device for a cell membrane according to claim 1, wherein the semiconductor refrigerator further comprises:
    a heat dissipating member disposed on a side of the second insulating substrate away from the first insulating substrate.

12. The culture device for a cell membrane according to claim 1, wherein the semiconductor refrigerator is disposed separately from the one or more culture vessels.

13. A preparation method for a cell membrane based on a culture device for a cell membrane, wherein the culture device for the cell membrane comprises:
    a semiconductor refrigerator comprising a first insulating substrate, a second insulating substrate, and at least one semiconductor thermocouple disposed between the first insulating substrate and the second insulating substrate, wherein the at least one semiconductor thermocouple comprises N semiconductor thermocouples, where N is an integer greater than or equal to 2, wherein: each of the N semiconductor thermocouples comprises a first semiconductor portion and a second semiconductor portion of different conductive types, wherein each of the first semiconductor portion and the second semiconductor portion comprises a first surface and a second surface opposite to the first surface, the first surface is closer to the first insulating substrate than the second surface, and the first surface of the first semiconductor portion is connected to the first surface of the second semiconductor portion via a first metal member, and the second surface of the first semiconductor portion of the i-th semiconductor thermocouple is connected to the second surface of the second semiconductor portion of the (i+1)-th semiconductor thermocouple via a second metal member, wherein $1 \leq i \leq N-1$; and
    one or more culture vessels disposed on a side of the first insulating substrate away from the second insulating substrate, a temperature-sensitive polymer layer is disposed on one surface of a bottom, away from the first insulating substrate, of at least one of the one or more culture vessels, wherein a surface energy of the temperature-sensitive polymer layer changes monotonously with changing temperature;
    wherein the semiconductor refrigerator further comprises a first switch, a first power supply, and a second power supply, wherein:
    a first pole of the first power supply is connected to the second surface of the second semiconductor portion of a first semiconductor thermocouple via a third metal member, and a second pole of the first power supply is configured to be connected to the second surface of the first semiconductor portion of an N-th semiconductor thermocouple via the first switch and a fourth metal member, wherein one of the first pole and the second pole is a positive pole and the other is a negative pole;
    the second pole of the second power supply is connected to the second surface of the second semiconductor portion of the first semiconductor thermocouple via the third metal member, and the first pole of the second power supply is configured to be connected to the second surface of the first semiconductor portion of the N-th semiconductor thermocouple via the first switch and the fourth metal member; and
    the first switch is configured to be connected to one of the second pole of the first power supply and the first pole of the second power supply in response to a user operation;
    the preparation method comprises:
    adjusting the first insulating substrate to be of a first temperature to make a plurality of cells in at least one of the one or more culture vessels form the cell membrane adsorbed to the temperature-sensitive polymer layer; and
    adjusting the first insulating substrate to be of a second temperature different from the first temperature to make the formed cell membrane separate from the temperature-sensitive polymer layer.

14. The preparation method according to claim 13, wherein the second temperature is less than the first temperature.

15. A preparation method for a cell membrane based on a culture device for a cell membrane, wherein the culture device for the cell membrane comprises:
a semiconductor refrigerator comprising a first insulating substrate, a second insulating substrate, and at least one semiconductor thermocouple disposed between the first insulating substrate and the second insulating substrate, wherein the at least one semiconductor thermocouple comprises N semiconductor thermocouples, where N is an integer greater than or equal to 2, wherein: each of the N semiconductor thermocouples comprises a first semiconductor portion and a second semiconductor portion of different conductive types, wherein each of the first semiconductor portion and the second semiconductor portion comprises a first surface and a second surface opposite to the first surface, the first surface is closer to the first insulating substrate than the second surface, and the first surface of the first semiconductor portion is connected to the first surface of the second semiconductor portion via a first metal member, and the second surface of the first semiconductor portion of the i-th semiconductor thermocouple is connected to the second surface of the second semiconductor portion of the (i+1)-th semiconductor thermocouple via a second metal member, wherein $1 \leq i \leq N-1$; and
one or more culture vessels disposed on a side of the first insulating substrate away from the second insulating substrate;
wherein the semiconductor refrigerator further comprises a first switch, a first power supply, and a second power supply, wherein:
a first pole of the first power supply is connected to the second surface of the second semiconductor portion of a first semiconductor thermocouple via a third metal member, and a second pole of the first power supply is configured to be connected to the second surface of the first semiconductor portion of an N-th semiconductor thermocouple via the first switch and a fourth metal member, wherein one of the first pole and the second pole is a positive pole and the other is a negative pole;
the second pole of the second power supply is connected to the second surface of the second semiconductor portion of the first semiconductor thermocouple via the third metal member, and the first pole of the second power supply is configured to be connected to the second surface of the first semiconductor portion of the N-th semiconductor thermocouple via the first switch and the fourth metal member; and
the first switch is configured to be connected to one of the second pole of the first power supply and the first pole of the second power supply in response to a user operation;
the preparation method comprises:
forming a temperature-sensitive polymer layer on one surface of a bottom, away from the first insulating substrate, of at least one of the one or more culture vessels, wherein a surface energy of the temperature-sensitive polymer layer changes monotonously with changing temperature;
adjusting the first insulating substrate to be of a first temperature to make a plurality of cells in at least one of the one or more culture vessels form the cell membrane adsorbed to the temperature-sensitive polymer layer; and
adjusting the first insulating substrate to be of a second temperature different from the first temperature to make the formed cell membrane separate from the temperature-sensitive polymer layer.

16. The preparation method according to claim 15, wherein the second temperature is less than the first temperature.

* * * * *